United States Patent
Au et al.

(10) Patent No.: US 6,821,302 B2
(45) Date of Patent: Nov. 23, 2004

(54) PERMANENT COLORING OF HAIR USING CARBONATE SALTS AND BICARBONATE SALTS AND USING PERCARBAMIC ACID PRECURSORS

(75) Inventors: Van Au, New City, NY (US); Stephen Alan Madison, New City, NY (US); John Brian Bartolone, Bridgeport, CT (US)

(73) Assignee: Unilever Home & Personal Care USA, Division of Conopco, Inc., Chicago, IL (US)

( * ) Notice: Subject to any disclaimer, the term of this patent is extended or adjusted under 35 U.S.C. 154(b) by 239 days.

(21) Appl. No.: 10/286,255

(22) Filed: Nov. 1, 2002

(65) Prior Publication Data

US 2004/0083557 A1 May 6, 2004

(51) Int. Cl.⁷ .................................................. A61K 7/13
(52) U.S. Cl. ................. 8/405; 8/406; 8/408; 8/410; 8/411; 8/412; 8/421; 8/424; 8/582; 8/618
(58) Field of Search ........................ 8/405, 406, 408, 8/410, 411, 412, 421, 424, 582, 618

(56) References Cited

U.S. PATENT DOCUMENTS

| 4,756,845 A | 7/1988 | Sugawara et al. | 252/102 |
| 5,131,912 A | 7/1992 | Ehara et al. | 8/408 |
| 5,525,123 A | 6/1996 | Lorenz et al. | 8/408 |
| 5,876,465 A | 3/1999 | Terranova et al. | 8/409 |
| 2004/0055092 A1 * | 3/2004 | Lewis et al. | 8/115.51 |

FOREIGN PATENT DOCUMENTS

WO  02/16538 A1  2/2002

OTHER PUBLICATIONS

Copending application: Ser. No. 09/811,920, Patel et al., filed Mar. 19, 2001, Method and Composition for Gradual Permanent Coloring of Hair.
International Search Report.

* cited by examiner

Primary Examiner—Yogendra N. Gupta
Assistant Examiner—Eisa Elhilo
(74) Attorney, Agent, or Firm—Karen E. Klumas

(57) ABSTRACT

Compositions and methods for achieving permanent hair color change which composition includes a mixture of:
 a) a composition A which comprises:
  i) at least one oxidation hair dye precursor;
  ii) a metal cyanate selected from the group consisting of KOCN, NaOCN, LiOCN, $Ca(OCN)_2$, $Mg(OCN)_2$, $Zn(OCN)_2$ and mixtures thereof which comprises a cyanate ion at about 0.1 to about 2.5%; and
  iii) an alkalizing agent;
 b) and a composition B which comprises:
  i) an oxidizing compound;
wherein the mixture of composition A and composition B has a pH of about 7 to about 11;
are described.

14 Claims, No Drawings

PERMANENT COLORING OF HAIR USING CARBONATE SALTS AND BICARBONATE SALTS AND USING PERCARBAMIC ACID PRECURSORS

BACKGROUND OF THE INVENTION

The present invention relates to methods and compositions which provide permanent hair color, good color lifting, and which minimize hair damage. The methods and compositions of the invention also do not require ammonia. Without the pungent odor of ammonia, the compositions of the invention are more appealing to the consumer.

Permanent hair color conventionally comes in two parts: a dye solution and a developer solution. In a conventional permanent hair coloring treatment, the dye solution and the developer solution, which includes a peroxide compound and a basifying compound such as ammonia, are mixed and then applied to the hair, which is then left for about 25 to about 35 minutes. The hair is then rinsed with water, treated with a post treatment conditioner, and then rinsed again with water.

The application of the dye solution and the developer solution affords permanent hair coloring. The odor of ammonia is also not appealing to the consumer. It would be desirable to develop methods and compositions for permanently coloring hair that minimize the hair damage that is caused and lack the odor of ammonia.

Patents and patent applications related to the field of this invention are as follows:

Canadian Patent No. 2083319 discloses a process for improving the degree of whiteness of chlorine-free prebleached woodpulp, in which an alkali metal cyanate is use with hydrogen peroxide in a further bleaching step.

U.S. Pat. No. 5,131,912 discloses durable 2-part hair dyeing agents composed of a first agent comprising as essential components at least one compound that forms $HCO_3$—by dissociation in water, an alkali generating substantially no irritating odor and a dye for hair and having a pH of 8.2 to 9.0, and a second agent comprising as essential components hydrogen peroxide and a buffer solution and having a pH of 2.0 to 4.0, the weight ratio of the first agent and the second agent to be mixed being such that the pH of the mixture of the two is in a range of from 6.5 to 7.9. These 2-part hair dyeing agents require only a short dyeing time, create little damage to hair and no irritating or disagreeable odor and have high dyeing effect.

U.S. Pat. No. 5,525,123, discloses a hair dyeing composition based on oxidation dyestuff precursors which dyes and brightens the hair containing, besides at least one developing and at least one coupling agent, at least one metal salt and at least one ammonium compound selected from the group ammonium chloride, ammonium sulfate, ammonium carbonate, ammonium bicarbonate, and ammonium carbamate, having a pH-value between 8 and 11, preferably from 9 to 10, after admixture with an oxidizing agent in the ready-to-use preparation.

Co-owned and co-pending Ser. No. 09/811,920 filed Mar. 19, 2001 discloses a method for permanently dyeing hair which comprises subjecting said hair to a number of treatments, having a set time interval between each two consecutive such treatments, wherein each treatment comprises steps a.) and b.) below:

a.) contacting said hair, for a period of about 5 seconds to about 5 minutes with a recently made mixture of:

i) an alkaline composition comprising a dye intermediate in a shampoo base or in a conditioner base; and ii) an acidic composition comprising an oxidating compound in a shampoo base or in a conditioner base;

b.) rinsing said mixture from said hair with water;

with the proviso that when a conditioner base is present in a.) i.) above, an independently selected conditioner base is also present in a.) ii.) above; and when a shampoo base is present in a.) i.) above, an independently selected shampoo base is also present in a.) ii.) above;

and wherein said number of treatments is between about 2 to about 30; and wherein said set time interval between each two consecutive treatments is between about 8 hours and 30 days, is described.

WO 02/16538 discloses a method of treatment of a material, comprising contacting said material with a percarbamic acid and/or diacyl percarbamate.

U.S. Pat. No. 4,756,845 discloses a bleaching agent composition comprising a peroxide capable of releasing hydrogen peroxide in aqueous solution, in admixture with an activator for the peroxide selected from the group consisting of naphthonitriles, isophthalonitrides, terephthalonitriles, alkali metal salts of cyanic acid, cyanic acid ammonium salt, cyanopyridines and acid neutralized products thereof, cyanopyridinium salts, O-acyl compounds, and N-acyl compounds has improved bleaching power and enables bleaching of an article within a short period of time.

SUMMARY OF THE INVENTION

The invention relates to compositions and methods for achieving permanent hair color change wherein said composition includes a mixture of:

which composition includes a mixture of:

a) a composition A which comprises:
   i) at least one oxidation hair dye precursor;
   ii) a metal cyanate selected from the group consisting KOCN, NaOCN, LiOCN, $Ca(OCN)_2$, $Mg(OCN)_2$, $Zn(OCN)_2$ and mixtures thereof which comprises a cyanate ion at about 0.1 to about 2.5%; and
   iii) an alkalizing agent;
b) and a composition B which comprises:
   i) an oxidizing compound;

wherein the mixture of composition A and composition B has a pH of about 7 to about 11.

The present invention also relates to a method for coloring hair which comprises contacting the hair with a mixture of composition A and composition B.

DETAILED DESCRIPTION OF THE INVENTION

As used herein, "the mixture of composition A and composition B", means a mixture of composition A and composition B. It is understood, of course, that a mixture of composition A and composition B is made according to the process of the present invention by first contacting the hair with composition A, then waiting for about 5 to about 60 minutes, and then contacting the hair with composition B. Accordingly, the mixture of A and B is made in the hair. As used herein % means weight % unless otherwise indicated. When used herein % refers to weight % as compared to the total weight of the composition that is being discussed. For example, when % is used to discuss the amount of an ingredient that is in the hair colorant part or hair dye precursor part composition A, this means weight % as compared to the total weight of composition A. When weight % of a composition comprising an oxidizing agent that is composition B, is mentioned, this means the weight % as compared to the total weight of composition B. However, when the following words are used, "a metal cyanate selected from the group consisting of KOCN, NaOCN, LiOCN, $Ca(OCN)_2$, $Mg(OCN)_2$, $Zn(OCN)_2$ and mixtures thereof which comprises a cyanate ion at about 0.1 to about 2.5%" or some other stated concentration, the concentration of cyanate ion is relative to the mixture of composition A and composition B. When the ratio of composition A to composition B is discussed this means the ratio of weight % of composition A to composition B. As used herein "inactive" or "substantially inactive" means that the oxidation hair dye precursors are not chemically reacting so as to form coupled or polymerized hair color molecules, or it means that the oxidation hair dye precursors are not chemically reacting in a substantial manner so as to form coupled or polymerized hair color molecules. Hair colorant or hair dye precursor compositions of the invention means compositions which comprise oxidation hair dye precursors capable of reacting, coupling, or polymerizing to form hair color molecules. "Hair colorant compositions of the invention" are used interchangeably with "hair coloring compositions" of the invention or "coloring compositions of the invention" or "hair dye precursor compositions" or "composition A". "Hair color developer compositions of the invention" are used interchangeably with "developer compositions" of the invention "compositions comprising an oxidizing agent" or "composition B". As used herein the term "recently" means within a very short interval of time such as within a few seconds or minutes, such as within 0.01 seconds to 120 seconds, or within 0.1 seconds to 60 seconds, or within 0.5 second to within 30 second or within 2 seconds to within 20 seconds. As used herein "metathetical" means chemically interchangeable. For example, a mixture of $NH_4Cl$ and $NaHCO_3$ is metathetical with a mixture of $(NH_4)HCO_3$ and NaCl. Compositions of the invention may be made by means which are known in the art or which are analogous to those which are known in the art. Ingredients which are included in compositions of the invention are known in the art or may be made by means which are known in the art.

The invention relates to compositions and methods for achieving permanent hair color change wherein said composition includes a mixture of:

which composition includes a mixture of:

a) a composition A which comprises:
  i) at least one oxidation hair dye precursor;
  ii) a metal cyanate selected from the group consisting of KOCN, NaOCN, LiOCN, $Ca(OCN)_2$, $Mg(OCN)_2$, $Zn(OCN)_2$ and mixtures thereof which comprises a cyanate ion at about 0.1 to about 2.5%; and
  iii) an alkalizing agent;
b) and a composition B which comprises:
  i) an oxidizing compound;

wherein the mixture of composition A and composition B has a pH of about 7 to about 11.

Composition A of the compositions of the invention may comprise:
  i) about 0.001 to about 7.0% of at least one oxidation hair dye precursor; and
  ii) an aqueous carrier.

Composition A of the compositions of the invention may preferably comprise:
  i) about 0.001 to about 5.0% of at least one oxidation hair dye precursor; and
  ii) an aqueous carrier.

The pH of composition A may be about 4 to about 11 or more preferably about 6 to about 8. Composition A may further comprise surfactants, chelators, hair swelling agents, viscosity modifiers, buffering agents, and the like.

Composition B of the compositions of the invention may comprise:
  i) about 0.001 to about 10.0% of an oxidizing agent or compound such as hydrogen peroxide.

Composition B of the compositions of the invention may preferably comprise:
  i) about 4.0 to about 9.0% of an oxidizing agent or compound such as hydrogen peroxide; and an aqueous carrier and The pH of composition B may be about 3 to about 7 or more preferably about 3.2 to about 6.5, or about 4.0 to 6.5. Composition B may further comprise thickening agents, buffering agents, and the like.

What follows is a description of the ingredients that can be included in the compositions of the present invention.

First, there are described ingredients that can be included in composition A of the invention.

Oxidative Hair Dye Precursors or Hair Dye Precursors

The hair colorant compositions of the present invention include one or more oxidative hair coloring agents, precursors or dyes. Such oxidative hair-coloring agents are used in combination with the oxidizing systems of the present invention to deliver permanent hair dye to the hair.

Permanent hair dye compositions as defined herein are compositions, which once applied to the hair, are substantially resistant to washout.

The dye forming intermediates used in oxidative hair dyes can be aromatic diamines, naphthols, aminophenols and their derivatives. These dye forming intermediates can be classified as; primary and secondary intermediates, couplers and modifiers. Primary intermediates are chemical compounds, which by themselves will form a dye upon oxidation. The secondary intermediates, also known as color modifiers or couplers, are used with other intermediates for specific color effects or to stabilize the color.

The oxidation dye intermediates, which are suitable for use in the compositions and processes herein, include aromatic diamines, naphthols, polyhydric phenols, aminophenols and derivatives of these aromatic compounds (e.g., N-substituted derivatives of the amines, and ethers of the phenols). Primary oxidation dye intermediates are generally colorless molecules prior to oxidation. The oxidation dye color is generated when the primary intermediate is 'activated' and subsequently joined with a secondary intermediate (coupling agent), which is also generally colorless, to form a colored, conjugated molecule. In general terms, oxidation hair dye precursors or intermediates include those monomeric materials which, on oxidation, form oligomers or polymers having extended conjugated systems of electrons in their molecular structure. Because of the new electronic structure, the resultant oligomers and polymers exhibit a shift in their electronic spectra to the visible range and appear colored. For example, oxidation dye precursors capable of forming colored polymers include materials such as aniline, which has a single functional group and which, on oxidation, forms a series of conjugated imines and quinoid dimers, trimers, etc. ranging in color from green to black. Compounds such as p-phenylenediamine, which has two functional groups, are capable of oxidative polymerization to yield higher molecular weight colored materials having extended conjugated electron systems. Color modifiers (couplers), such as those detailed hereinafter, are preferably used in conjunction with the oxidation dye precursors herein and are thought to interpose themselves in the colored polymers during their formation and to cause shifts in the electronic spectra thereof, thereby resulting in slight color changes. A representative list of oxidation dye precursors suitable for use herein is found in Sagarin, "Cosmetic Science and Technology", Interscience, Special Edition, Volume 2, pages 308 to 310 which is herein incorporated by reference.

It is to be understood that oxidizing aids of the present invention are suitable for use (in combination with a source of peroxide as detailed herein) with all manner of oxidation dye precursors and color modifiers and that the precursors detailed below are only by way of example and are not intended to limit the compositions and processes herein.

The typical aromatic diamines, polyhydric phenols, aminophenols, and derivatives thereof, described above as primary dye precursors can also have additional substituents on the aromatic ring, e.g. halogen, aldehyde, carboxylic additional substituents on the amino nitrogen and on the phenolic oxygen, e.g. substituted and unsubstituted alkyl and aryl groups.

The hair coloring compositions of the present invention may, in addition to the essential oxidative hair-coloring agents, optionally include non-oxidative and other dye materials. Optional non-oxidative and other dyes suitable for use in the hair coloring compositions and processes according to the present invention include semipermanent, temporary and other dyes. Non-oxidative dyes as defined herein include the so-called 'direct action dyes', metallic dyes, metal chelate dyes, fiber reactive dyes and other synthetic and natural dyes. See Chemical and Physical Behaviour of Human Hair 3rd Edn., by Clarence Robbins (pp 250–259); 'The Chemistry and Manufacture of Cosmetics'. Volume IV. 2nd Edn. Maison G. Various types of non-oxidative dyes are detailed in: 'Navarre at chapter 45 by G. S. Kass (pp 841–920); 'Cosmetics: Science and Technology' 2nd Edn, Vol. II Balsam Sagarin, Chapter 23 by F. E. Wall (pp 279–343); 'The Science of Hair Care' edited by C. Zviak, Chapter 7 (pp 235–261) and 'Hair Dyes', J. C. Johnson, Noyes Data Corp., Park Ridge, U.S.A. (1973), (pp 3–91 and 113–139).

Specific hair dyes which may be included in the compositions of the invention include m-aminophenol, p-phenylene diamine, p-toluenediamine; p-phenylenediamine; 2-chloro-p-phenylenediamine; N-phenyl-p-phenylenediamine; N-2-methoxyethyl-p-phenylenediamine; N,N-bis-(hydroxyethyl)-p-phenylenediamine; 2-hydroxymethyl-p-phenylenediamine; 2-hydroxyethyl-p-phenylenediamine; 4,4'-diaminodiphenylamine; 2,6-dimethyl-p-phenylenediamine; 2-isopropyl-p-phenylenediamine; N-(2-hydroxypropyl)-p-phenylenediamine; 2-propyl-p-phenylenediamine; 1,3-N,N-bis-(2-hydroxyethyl)-N,N-bis (4-aminophenyl)-2-propanol; 2-methyl-4-dimethylaminoaniline; p-aminophenol; p-methylaminophenol; 3-methyl-p-aminophenol; 2-hydroxymethyl-p-aminophenol; 2-methyl-p-aminophenol; 2-(2-hydroxyethylaminomethyl)-p-aminophenol; 2-methoxymethyl-p-aminophenol; and 5-aminosalicylic acid; catechol; pyrogallol; o-aminophenol; 2,4-diaminophenol; 2,4,5-trihydroxytoluene; 1,2,4-trihydroxybenzene; 2-ethylamino-p-cresol; 2,3-dihydroxynaphthalene; 5-methyl-o-aminophenol; 6-methyloaminophenol; and 2-amino-5-acetaminophenol; 2-methyl-1-naphthol; 1-acetoxy-2-methylnaphthalene; 1,7-dihydroxynaphthalene; resorcinol; 4-chlororesorcinol; 1-naphthol; 1,5-dihydroxynaphthalene; 2,7-dihydroxynaphthalene; 2-methylresorcinol; 1-hydroxy-6-aminonaphthalene-3-sulfonic acid; thymol (2-isopropyl-5-methylphenol); 1,5-dihydroxy-1,2,3,4-tetrahydronaphthalene; 2-chlororesorcinol; 2,3-dihydroxy-1,4-naphthoquinone; and 1-naphthol-4-sulfonic acid; m-phenylenediamine; 2-(2,4-diaminophenoxy)ethanol; N,N-bis(hydroxyethyl)-m-phenylenediamine; 2,6-diaminotoluene; N,N-bis(hydroxyethyl)-2,4-diaminophenetole; bis(2,4-diaminophenoxy)-1,3-propane; 1-hydroxyethyl-2,4-diaminobenzene; 2-amino-4 hydroxyethylaminoanisole; aminoethoxy-2,4-diaminobenzene; 2,4-diaminophenoxyacetic acid; 4,6-bis(hydroxyethoxy)-m-phenylenediamine; 2,4-diamino-5-methylphenetole; 2,4-diamino-5-hydroxyethoxytoluene; 2,4-dimethoxy 1,3-diaminobenzene; and2,6-bis(hydroxyethylamino)toluene; m-aminophenol; 2-hydroxy-4-carbamoylmethylaminotoluene; m-carbamoylmethylaminophenol; 6-hydroxybenzomorpholine; 2-hydroxy-4-aminotoluene; 2-hydroxy-4-hydroxyethylaminotoluene; 4,6-dichloro-m-aminophenol; 2-methyl-m-aminophenol;2-chloro-6-methyl-m-aminophenol; 2-hydroxyethoxy-5-aminophenol; 2-chloro-5-trifluoroethylaminophenol; 4-chloro-6-methyl-m-aminophenol; N-cyclopentyl-3-aminophenol; N-hydroxyethyl-4-methoxy-2-methyl-m-aminophenol and 5-amino-4-methoxy-2-methylpheno; 2-dimethylamino-5-aminopyridine; 2,4,5,6-tetra-aminopyrimidine; 4,5-diamino-1-methylpyrazole; 1-phenyl-3-methyl-5-pyrazolone; 6-methoxy-8-aminoquinoline; 2,6-dihydroxy-4-methylpyridine; 5-hydroxy-1,4-benzodioxane; 3,4-methylenedioxyphenol; 4-hydroxyethylamino-1,2-methylenedioxybenzene; 2,6-dihydroxy-3,4-dimethylpyridine; 5-chloro-2,3-dihydroxypyridine; 3,5-diamino-2,6-dimethoxypyridine; 2-hydroxyethylamino-6-methoxy-3-aminopyridine; 3,4-methylenedioxyaniline; 2,6-bis-hydroxyethoxy-3,5-diaminopyridine; 4,3-amino-5-hydroxy-2,6-dimethoxypyridine; 5,6-dihydroxyindole; 7-hydroxyindole; 5-hydroxyindole; 2-bromo-4,5-methylenedioxyphenol; 6-hydroxyindole; 3-amino-2-methylamino-6-methoxypyridine; 2-amino-3-hydroxypyridine; 2,6-diaminopyridine; 5-(3,5-diamino-2-pyridyloxy)-1,3-dihydroxypentane; 3-(3,5-diamino-2-pyridyloxy)-2-hydroxypropanol and 4-hydroxy-2,5,6-triaminopyrimidine, 4,6-dimethoxy-3-amino-1-hydroxybenzene; 2,6-dimethyl-4-(p-hydroxyphenyl)amino] phenol; 4-benzylnaphth-1-ol; 4-chloronaphth-1-ol; 4-chloro-5,8-dimethoxy-6-methyinaphth-1-ol, 4-chloro-5,8-dimethoxynaphth-1-ol; 4-acetoxy-5-chloro-6-methyl-7-acetyl-8-hydroxynaphth-1-ol; 4-acetoxy-6-methyl-7-acetyl-8-hydroxynaphth-1-ol, 4-acetoxy-8-benzyloxynaphth-1-ol; 4-benzyloxynaphth-1-ol, 4,8-dibenzyloxy-6-methylnaphth-1-ol; 4,8-dibenzyloxynaphth-1-ol, 4-benzyloxy-8-(2-chloro) ethoxynaphth-1-ol; 4-benzyloxy-8-isopropyloxynaphth-1-ol, 4-benzyloxy-8-methoxynaphth-1-ol; 4-(2,2,2-trifluoroethoxy)naphth-1-ol, 4-(2-bromo)ethoxynaphth-1-ol; 4-(2-bromo)ethoxy-5-methoxynaphth-1-ol, 4-(2-bromo) ethoxy-8-methoxynaphth-1-ol; 4-(2-chloro)ethoxynaphth-1-ol, 4-(2-chloro)ethoxy-8-methoxynaphth-1-ol; 4-(2-methoxy)ethoxynaphth-1-ol, 4-(1,4,7-trioxaheptyl)naphth-1-ol; 4-(1,4,7-trioxaoctyl)naphth-1-ol, 4-(1,4,7,10- tetraoxadecyl)naphth-1-ol; (4-hydroxy-1-naphthyl) oxyacetic acid, 4-methoxynaphth-1-ol; 4-methoxy-5-chloronaphth-1-ol, 4-methoxy-5-chloro-8-benzyloxynaphth-1-ol; 4,8-dimethoxy-5-chloronaphth-1-ol, 4-methoxy-5-methyinaphth-1-ol; 4-methoxy-5-benzyloxynaphth-1-ol, 4-methoxy-5-benzyloxy-7-methylnaphth-1-ol; 4-methoxy-5-hydroxynaphth-1-ol, 4-methoxy-5-hydroxy-7-methylnaphth-1-ol; 4-methoxy-5-isopropyloxynaphth-1-ol, 4,5-dimethoxynaphth-1-ol; 4,5-dimethoxy-6-benzyloxynaphth-1-ol, 4,5-dimethoxy-7-methyinaphth-1-ol; 4,5-dimethoxy-8-chloronaphth-1-ol, 4-methoxy-6-methyinaphth-1-ol; 4-methoxy-6-methyl-7-acetyl-8-hydroxynaphth-1-ol, 5-4-methoxy-6,7-dimethylnaphth-1-ol; 4-methoxy-6-methyl-8-benzyloxynaphth-1-ol, 4-methoxy-6-methyl-8-hydroxynaphth-1-ol; 4,8-dimethoxy-6-methylnaphth-1-ol, 4-methoxy-6-ethoxynaphth-1-ol; 4-methoxy-6,7-diethoxynaphth-1-ol, 4-methoxy-7-methyinaphth-1-ol; 4,8-dimethoxy-7-benzyloxynaphth-1-ol, 4-methoxy-7-ethoxynaphth-1-ol; 4-methoxy-8-chloronaphth-1-ol, 4-methoxy-8-methyinaphth-1-ol; 4-methoxy-8-benzyloxynaphth-1-ol, 4-methoxy-8-hydroxynaphth-1-ol; 4-methoxy-8-isopropyloxynaphth-1-ol, 4,8-dimethoxynaphth-1-ol; 4-ethoxynaphth-1-ol, 4-propyloxynaphth-1-ol; 4-isopropyloxynaphth-1-ol, 4-butoxynaphth-1-ol; 4-isobutoxynaphth-1-ol, 4-sec-butoxynaphth-1-ol; 4-isoamoxynaphth-1-ol; 4-bis(2-chloroisopropyloxy)naphth-1-ol; 4-cyclohexyloxynaphth-1-ol; 4-octyloxynaphth-1-ol; 4-(2-chloropropoxy)naphth-1-ol; isopropylidene-4,5-dioxynaphth-1-ol; 5-methoxynaphth-1-ol; 5,8-dimethoxy-6-methylnaphth-1-ol; 5,8-dimethoxy-6,7-dichloronaphth-1-ol; 5,8-dimethoxy-7-methyinaphth-1-ol; 5,8-diacetoxynaphth-1-ol; 8-methoxynaphth-1-ol; 4-methoxynaphth-1-ol; 4-ethoxynaphth-1-ol; 4-isopropyloxynaphth-1-ol; 4,8-dimethoxynaphth-1-ol and salts thereof or combinations thereof.

Precursor of Percarbamic Acid Which Comprises Cyanate Ion

Composition A of the present invention comprises a percarbamic acid precursor which may be a salt or an organic compound containing a cyanate ion. Salts which contain a cyanate ion may be selected from a metal cyanate selected from the group consisting of KOCN, NaOCN, LiOCN, $Ca(OCN)_2$, $Mg(OCN)_2$, $Zn(OCN)_2$ and mixtures thereof. A most preferable percarbamic acid precursor is NaOCN.

A precursor of percarbamic acid may also include any compound which has a half life of at least about 2 months, more preferably at least about 4 months, in a solution having a pH between about 9 and about 10, at approximately 25° C.; and wherein at least about 5% of the cyanate ion is consumed, in about 45 minutes, in the presence of hydrogen peroxide, wherein said hydrogen peroxide is present at a concentration of about 8% to about 10% for example. Such a precursor of percarbamic acid may include organic compounds.

Metal Bicarbonate Salt

Composition A of the invention may comprise a metal bicarbonate that is an agent that forms $HCO_3$ by dissociation in water, such as $Na_2CO_3$, $NaHCO_3$, $K_2CO_3$, $KHCO_3$, $CaCO_3$, $MgCO_3$ and $Ca(HCO_3)_2$. These compounds may be used singly or, in combination.

Surfactants

Composition A of the present invention may additionally contain a surfactant system. Suitable surfactants for inclusion in the compositions of the invention generally have a lipophilic chain length of from about 8 to about 22 carbon atoms and can be selected from the group consisting of anionic, cationic, nonionic, amphoteric, zwitterionic surfactants and mixtures thereof.

Buffering Agents

Buffering agents may be present in composition A and composition B of the present invention. Coloring compositions of the present invention may contain one or more hair swelling agents (HSAs) such as urea, to adjust the pH to the desired level. Several different pH modifiers can be used to adjust the pH of the final composition or any constituent part thereof.

Preferred for use as a buffering agent for the coloring compositions according to the present invention is sodium hydroxide.

In oxidizing and coloring kits comprising a portion of peroxide oxidizing agent, which may be present in either solid or liquid form, such as hydrogen peroxide, a buffering agent solution is required to stabilize hydrogen peroxide. Since hydrogen peroxide is stable in the pH range from 2 to 4, it is necessary to use a buffering agent having a pH within this range. Dilute acids are suitable hydrogen peroxide buffering agents. Phosphoric acid is a preferred agent for buffering hydrogen peroxide solutions.

This pH adjustment can be effected by using well known acidifying agents in the field of treating keratinous fibers, and in particular human hair, such as inorganic and organic acids such as hydrochloric acid, tartaric acid, citric acid, and carboxylic or sulphonic acids such as ascorbic acid, acetic acid, lactic acid, sulphuric acid, formic acid, and sodium dihydrogenphosphate/phosphoric acid, disodium hydrogen phosphate/phosphoric acid, potassium chloride/hydrochloric acid, potassium dihydrogen phthalate/hydrochloric acid, sodium citrate/hydrochloric acid, potassium dihydrogen citrate/hydrochloric acid, potassium dihydrogencitrate/citric acid, sodium citrate/citric acid, sodium tartarate/tartaric acid, sodium lactate/lactic acid, sodium acetate/acetic acid, disodium hydrogenphosphate/citric acid and sodium chloride/glycine/hydrochloric acid and mixtures thereof.

Solvents

Water is the preferred principal diluent or solvent for the compositions according to the present invention (that is, compositions A and B of the invention or mixtures thereof). As such, the compositions according to the present invention may include one or more solvents as additional diluent materials. Generally, the solvent is selected to be miscible with water and innocuous to the skin. Solvents suitable for use herein include $C_1$–$C_{20}$ mono- or polyhydric alcohols and their ethers, glycerine, with monohydric and dihydric alcohols and their ethers preferred. In these compounds, alcoholic residues containing 2 to 10 carbon atoms are preferred. Thus, a particularly preferred group includes ethanol, isopropanol, n-propanol, butanol, propylene glycol, ethylene glycol monoethyl ether, and mixtures thereof.

These solvents may be present in composition A and composition B of the invention.

Thickeners or Gelling Agents

Thickeners may be included in composition A and composition B of the invention. Long chain fatty alcohols having from about 11 to about 18 carbon atoms in the long fatty chain can be thickener constituents of compositions of this invention. These alcohols can be used alone, or in admixture with each other. When included in the compositions, the alcohol is preferably present at from about 0.5 to about 10 weight percent of the composition, and more preferably at from about 2 to about 5 weight percent.

Lauryl alcohol, oleyl alcohol, myristyl alcohol, stearyl alcohol, and the like, and mixtures thereof are contemplated herein. In addition, mixtures of natural or synthetic fatty alcohols having fatty chain lengths of from about 11 to about 18 carbons are also useful. Several such mixtures are available commercially, and are exemplified by the material containing a mixture of synthetic alcohols with 12 to 15 carbons in the alkyl chain sold under the trademark NEODOL 25 by Shell Chemical Company, and the material containing a mixture of synthetic alcohols with chain lengths of 12 to 16 carbons sold under the trademark ALFOL 1216 Alcohol by Conoco Chemicals.

Thickening agents suitable for use in the compositions herein may also be selected from oleic acid, cetyl alcohol, oleyl alcohol, sodium chloride, cetearyl alcohol, stearyl alcohol, synthetic thickeners such as Carbopol, Aculyn and Acrosyl and mixtures thereof. Preferred thickeners for use herein are Aculyn 22 (RTM), steareth-20 methacrylate copolymer; Aculyn 44 (RTM) polyurethane resin and Acusol 830 (RTM), acrylates copolymer that are available from Rohm and Haas, Philadelphia, Pa., USA. Additional thickening agents suitable for use herein include sodium alginate or gum arabic, or cellulose derivatives, such as methyl cellulose or the sodium salt of carboxymethylcellulose or acrylic polymers.

Fatty alcohols of the above discussed carbon chain lengths which are ethoxylated to contain an average of one or two moles of ethylene oxide per mole of fatty alcohol can be used in place of the fatty alcohols themselves. Examples of such useful ethoxylated fatty acids include ethylene glycol cetyl ether, polyoxyethylene (2) stearyl ether, and the like; the exemplary compounds having CTFA Dictionary names of Ceteth-1 and Steareth-2, respectively.

Volatile Silicones

Volatile silicones may also be employed in composition A and composition B of the invention. The volatile silicone oil is often described as a volatile polyorganosiloxane, and is a liquid material having a measurable vapour pressure at ambient conditions (about 20 to 25° C.). Typically the vapour pressure of volatile silicones lies in the range of from 1 or 10 Pa to 2 kPa at 25° C. Volatile polyorganosiloxanes can be linear or cyclic or mixtures thereof. Preferred cyclic siloxanes include polydimethylsiloxanes and particularly those containing from 3 to 9 silicon atoms and preferably not more than 7 silicon atoms and most preferably from 4 to 6 silicon atoms, otherwise often referred to as cyclomethicones. Preferred linear siloxanes include polydimethylsiloxanes containing from 3 to 9 silicon atoms. The volatile siloxanes normally by themselves exhibit viscosities of below $1 \times 10^{-5}$ m$^2$/sec (10 centistokes), and particularly above $1 \times 10^{-7}$ m$^2$/sec (0.1 centistokes), the linear siloxanes normally exhibiting a viscosity of below $5 \times 10^{-6}$ m$^2$/sec (5 centistokes). The volatile silicones can also comprise branched linear or cyclic siloxanes such as the aforementioned linear or cyclic siloxanes substituted by one or more pendant —O—Si(CH$_3$)$_3$ groups. Examples of commercially available silicone oils include oils having grade designations 344, 345, 244, 245 and 246, (from Dow Corning Corporation) Silicone 7207 and Silicone 7158 (from Union Carbide Corporation) and SF1202 (from General Electric [US]).

Non-Volatile Silicones

Non-volatile silicone oils may also be employed in composition A and composition B of the invention. Non-volatile silicone oils include polyalkyl siloxanes, polyalkylaryl siloxanes and polyethersiloxane copolymers. These can suitably be selected from dimethicone and dimethicone copolyols. Commercially available nonvolatile silicone oils include Dow Corning 556 and Dow Corning 200 series having a viscosity of at least 50 centistokes.

The essentially non-volatile polyalkyl siloxanes useful herein include, for example, polydimethyl siloxanes with viscosities of from about 5 to about 25 million centistokes at 25° C. Among the preferred non-volatile silicones useful in the present compositions are the polydimethyl siloxanes having viscosities from about 10 to about 400 centistokes at 25° C.

There will now be described ingredients that can be included in composition B of the invention.

Oxidizing Agents or Compounds

As used herein, oxidizing agent is interchangeable with oxidizing compound. The composition B of the invention may comprise at least one water-soluble peroxygen oxidizing agent. Water-soluble as defined herein means a peroxygen oxidizing agent, which can be substantially solubilized in water.

The peroxygen oxidizing agents useful herein are generally inorganic peroxygen materials capable of yielding hydrogen peroxide in an aqueous solution. Water-soluble peroxygen oxidizing compounds are well known in the art and include hydrogen peroxide, inorganic alkali metal peroxides such as sodium periodate and sodium peroxide and organic peroxides such as urea peroxide, melamine peroxide, and inorganic perhydrate salt oxidizing compounds, such as the alkali metal salts of perborates, percarbonates, perphosphates, persilicates, persulphates and the like. These inorganic perhydrate salts may be incorporated as monohydrates, tetrahydrates, and the like. Mixtures of two or more such oxidizing agents can be used if desired. Preferred for use in composition B according to the present invention is hydrogen peroxide.

Composition B may also comprise a thickening agent, a surfactant, a chelator, a buffering agent, and the like.

Optional Ingredients

The compositions of the present invention that is compositions A and B can comprise a wide range of optional ingredients. The ingredients can fall into the following functional classes: anticaking agents, antioxidants, binders, biological additives, bulking agents, chelating agents, chemical additives, colorants, cosmetic astringents, cosmetic biocides, denaturants, drug astringents, emulsifiers, film formers, fragrance components, humectants, opacifying agents, plasticizers, preservatives, propellants, reducing agents, solvents, foam boosters, hydrotropes, solubilizing agents, suspending agents (nonsurfactant), sunscreen agents, ultraviolet light absorbers, and viscosity increasing agents (aqueous and nonaqueous). Examples of other functional classes of materials useful herein that are well known to one of ordinary skill in the art include solubilizing agents, sequestrants, and the like.

Other optional ingredients include organic acids. A non-exclusive list of examples of organic acids which can be used as the proton donating agent are adipic acid, tartaric acid, citric acid, maleic acid, malic acid, succinic acid, glycolic acid, glutaric acid, benzoic acid, malonic acid, salicylic acid, gluconic acid, polyacrylic acid, their salts, and mixtures thereof. Non-exclusive lists of examples of mineral acids for use herein are hydrochloric, phosphoric, sulfuric and mixtures thereof.

Assessment of Initial Color and Color Change

The equipment used to measure both the initial color and color change on substrates (hair) dyed with the hair coloring compositions of the present invention is a Hunter Colorquest spectrophotometer. The value used to express the degree of color change on any particular substrate is delta E (ΔE). Delta E, as defined herein, is represented by a factual sum of L, a, and b values such that:

$$\Delta E = (\Delta L^2 + \Delta a^2 + \Delta b^2)^{1/2}$$

and L is a measure of lightness and darkness (color intensity), wherein L=100 is equivalent to white, and L=0 is equivalent to black. Further, 'a' is a measure of the red and green quotients (color hues) such that positive equates to red and negative equates to green, and 'b', is a measure of the yellow and blue quotients (color hues) such that positive equates to yellow and negative equates to blue.

Compositions of the invention can be shown to cause a measurable change in hair color by the use of the just above described hair color change assessment method.

The following nonlimiting examples of the compositions of the invention were made by the procedure outlined below. A generic formulation for composition A of the invention.

| Dye Formulation Ingredients | |
|---|---|
| Chemical Name | % (w/w) |
| Hair dye precursors | 0.1–7 |
| | 0.5 |
| PEG3 Cocamine | 8 |
| Sodium carbonate | 0–5 |
| Sodium cyanate | 0.1–2 |
| NaOH to about pH 10 | |
| Water to balance | 100 |

FORMULA 1 which is composition A of the invention

| CHEMICAL NAME | % (w/w) |
|---|---|
| p-Phenylenediamine | 0.125 |
| m-Aminophenol | 0.0058 |
| Resorcinol | 0.133 |
| Phenyl-methyl-pyrazolone | 0.033 |
| N,N-bis-2-hydroxyethyl-PPD sulfate | 0.0125 |
| Sodium sulphite | 1 |
| Sodium EDTA | 0.6 |
| Sodium isoascorbate | 0.15 |
| Propylene glycol | 8.6 |
| Oleic acid (5 Titre) | 8.6 |
| Isopropanol | 12.5 |
| Perfume oil | 0.5 |
| Dihydroxyethyl soyamine dioleate | 22.2 |
| PEG3 Cocamine | 8 |
| Sodium carbonate | 6 |
| Sodium cyanate | 3 |
| NaOH to pH 10 | |
| Water to balance | 100 |

FORMULA 2 which is Composition of the Invention

| DYE FORMULATION INGREDIENTS CHEMICAL NAME | % (w/w) |
|---|---|
| p-Phenylenediamine | 1 |
| Resorcinol | 1 |
| Sodium sulphite | 1 |
| Sodium EDTA | 0.6 |
| Sodium isoascorbate | 0.15 |
| Propylene glycol | 12 |
| Oleic acid (5 Titre) | 8.6 |
| Isopropanol | 12.5 |
| Perfume oil | 0.5 |
| Dihydroxyethyl soyamine dioleate | 22.2 |
| PEG3 Cocamine | 8 |
| Sodium carbonate | 6 |
| Sodium cyanate | 3 |
| NaOH to pH 10 | |
| Water to balance | 100 |

FORMULA 3 which is Composition A of the Invention

| DYE FORMULATION INGREDIENTS CHEMICAL NAME | % w/w |
|---|---|
| 4-Aminophenol | 0.8 |
| 4-Amino-2-hydroxytoluene | 0.8 |
| Sodium sulphite | 1 |
| Sodium EDTA | 0.6 |
| Sodium isoascorbate | 0.15 |
| Propylene glycol | 12 |
| Oleic acid (5 Titre) | 8.6 |
| Isopropanol | 12.5 |
| Perfume oil | 0.5 |
| Dihydroxyethyl soyamine dioleate | 22.2 |
| PEG3 Cocamine | 8 |
| Sodium carbonate | 6 |
| Sodium cyanate | 3 |
| NaOH to pH 10 | |
| Water to balance | 100 |

A Generic Formulation for Composition B of the Invention.

| Developer Formulation | % w/w |
|---|---|
| Oxidizing agent | 0.01–10 |
| Water to balance | to 100 |

A Specific Formulation for Composition B of the Invention.

| Developer: Formulation Ingredients | |
|---|---|
| Chemical Name | % (w/w) |
| Ceteareth-7 | 1.00 |
| Polyquaternium-37 | 1.00 |
| 50% Hydrogen Peroxide | 12.00 |
| 85% Phosphoric Acid | 0.03% |
| Water to balance | q.s. 100 |

Preparation of Composition A of the Invention

Surfactants, perfume oil and solvent are mixed at 55° C. to obtain a homogenous solution (part 1). Deionized water is added to the beaker and mixing is continued. Antioxidants are added followed by solvent and nitrogen blanketing is begun. Dyes are added and the mixture is heated to 50–55° C. and further mixed until the solution is clear. The solution is cooled to 20–35° C. The solution pH is then adjusted to 9–12 with either concentrated ammonium hydroxide and/or 50% sodium hydroxide. Thereupon at least one percarbamic acid precursor and optionally a water soluble metal bicarbonate salt is added. After salt addition is complete the pH is again adjusted to be in the range 9.5–11. Optionally more water can be added.

Preparation of Composition B of the Invention

Add deionized water to beaker and begin mixing. Add surfactants, thickener and buffering agents follow by oxidizing agent and remaining ingredients to water.

In hair coloring kits which contain composition A and composition B of the present invention, a portion of peroxide oxidizing agent, may be present in either solid or liquid form, such as hydrogen peroxide in composition B, and an acid buffering agent solution as mentioned above may be required to stabilize the hydrogen peroxide, for example.

A dual package which can be employed in the products and kits of the present invention is disclosed in U.S. Pat. No. 6,082,588 to Markey et al which is hereby incorporated by reference.

Kit Containing an Instruction Sheet

The invention also relates to a kit for carrying out the hair coloring method of the invention. The kit may comprise compositions A and B each in a separate container as described herein. The kit also contains written instructions that explain how the compositions of the invention are used.

The consumer can admix the components of the kit according to written instructions, to obtain the aqueous reaction mixture. Because composition A and composition B react with each other, the hair must be contacted with a recently made mixture of composition A and composition B. After treatment for a desired time the mixture of A and B may be removed, preferably with water or a conventional shampoo or a conventional conditioning shampoo.

From the foregoing, it will be appreciated that although specific embodiments of the invention have been described herein for purposes of illustration, various modifications may be made without deviating from the spirit or scope of the invention.

What is claimed is:

1. A composition for achieving permanent hair color change comprises a mixture of:
   a) a composition A which comprises:
      i) at least one oxidation hair dye precursor;
      ii) a metal cyanate selected from the group consisting of KOCN, NaOCN, LiOCN, $Ca(OCN)_2$, $Mg(OCN)_2$, $Zn(OCN)_2$ and mixtures thereof which comprises a cyanate ion at about 0.1 to about 2.50%; and
      iii) an alkalizing agent; and
   b) a composition B which comprises:
      i) an oxidizing compound;
      wherein the mixture of composition A and composition B has a pH of about 7 to about 1.

2. The composition according to claim 1 wherein composition A comprises
   about 0.001 to about 7% of at least one oxidation hair dye precursor; and
   an aqueous carrier.

3. A The composition according to claim 1 wherein composition A comprises
   about 0.001 to about 5.0% of the at least one oxidation hair dye precursor; and
   an aqueous carrier.

4. The composition according to claim 1 wherein composition A comprises surfactants, chelators, hair swelling agents, viscosity modifiers, and buffering agents, and has a pH of about 4 to about 11.

5. The composition according to claim 1 wherein composition B comprises:
   about 0.001 to about 10.0% of the oxidizing agent or compound.

6. The composition according to claim 1 wherein composition B comprises:
   about 4.0 to about 9.0% of the oxidizing compound and an aqueous carrier and the pH of said composition B is about 3 to about 7.

7. The composition according to claim 1 wherein the oxidizing compound is hydrogen peroxide.

8. The composition according to claim 1 wherein compostion A further comprises a metal bicarbonate.

9. The composition according to claim 1 wherein the alkalizing agent comprises a metal bicarbonate selected from the group consisting of $Na_2CO_3$, $NaHCO_3$, $K_2CO_3$, $KHCO_3$, $CaCO_3$, $MgCO_3$ and $Ca(HCO_3)_2$ and mixtures thereof.

10. The composition according to claim 1 wherein the alkalizing agent is a metal bicarbonate at a concentration of about 0.1 to about 10%.

11. The composition according to claim 1 wherein the alkalizing agent is a metal bicarbonate at a concentration of about 2 to about 5%.

12. The composition according to claim 1 wherein the metal cyanate is Na OCN.

13. The composition according to claim 1, wherein said hair dye precursor is at least one compound selected from the group consisting of m-aminophenol; p-phenylene diamine; p-toluenediamine; p-phenylenediamine; 2-chloro-p-phenylenediamine; N-phenyl-p-phenylenediamine; N-2-methoxyethyl-p-phenylenediamine; N,N-bis-(hydroxyethyl)-p-phenylenediamine; 2-hydroxymethyl-p-phenylenediamine; 2-hydroxyethyl-p-phenylenediamine; 4,4'-diaminodiphenylamine; 2,6-dimethyl-p-phenylenediamine; 2-isopropyl-p-phenylenediamine; N-(2-hydroxypropyl)-p-phenylenediamine; 2-propyl-p-phenylenediamine; 1,3-N,N-bis-(2-hydroxyethyl)-N,N-bis(4-aminophenyl)-2-propanol; 2-methyl-4-dimethylaminoaniline; p-aminophenol; p-methylaminophenol; 3-methyl-p-aminophenol; 2-hydroxymethyl-p-aminophenol; 2-methyl-p-aminophenol; 2-(2-hydroxyethylaminomethyl)-p-aminophenol; 2-methoxymethyl-p-aminophenol; and 5-aminosalicylic acid; catechol; pyrogallol; o-aminophenol; 2,4-diaminophenol; 2,4,5-trihydroxytoluene; 1,2,4-trihydroxybenzene; 2-ethylamino-p-cresol; 2,3-dihydroxynaphthalene; 5-methyl-o-aminophenol; 6-methyl-o-aminophenol; 2-amino-5-acetaminophenol; 2-methyl-1-naphthol; 1-acetoxy-2-methylnaphthalene; 1,7-dihydroxynaphthalene; resorcinol; 4-chlororesorcinol; 1-naphthol; 1,5-dihydroxynaphthalene; 2,7-dihydroxynaphthalene; 2-methylresorcinol; 1-hydroxy-6-aminonaphthalene-3-sulfonic acid; thymol (2-isopropyl-5-methylphenol); 1,5-dihydroxy-1,2,3,4-tetrahydronaphthalene; 2-chlororesorcinol; 2,3-dihydroxy-1,4-naphthoquinone; 1-naphthol-4-sulfonic acid; m-phenylenediamine; 2-(2,4-diaminophenoxy)ethanol; N,N-bis(hydroxyethyl)-m-phenylenediamine; 2,6-diaminotoluene; N,N-bis(hydroxyethyl)-2,4-diaminophenetole; bis(2,4-diaminophenoxy)-1,3-propane; 1-hydroxyethyl-2,4-diaminobenzene; 2-amino-4 hydroxyethylaminoanisole; aminoethoxy-2,4-diaminobenzene; 2,4-diaminophenoxyacetic acid; 4,6-bis(hydroxyethoxy)-m-phenylenediamine; 2,4-diamino-5-methylphenetole; 2,4-diamino-5-hydroxyethoxytoluene; 2,4-dimethoxy 1,3-diaminobenzene; and 2,6-bis(hydroxyethylamino) toluene; m-aminophenol; 2-hydroxy-4-carbamoylmethylaminotoluene; m-carbamoyl methylaminophenol; 6-hydroxybenzomorpholine; 2-hydroxy-4-aminotoluene; 2-hydroxy-4-hydroxyethylaminotoluene; 4,6-dichloro-m-aminophenol; 2-methyl-m-aminophenol; 2-chloro-6-methyl-m-aminophenol; 2-hydroxyethoxy-5-aminophenol; 2-chloro-5-trifluoroethylaminophenol; 4-chloro-6-methyl-m-aminophenol; N-cyclopentyl-3-aminophenol; N-hydroxyethyl-4-methoxy-2-methyl-m-aminophenol and 5-amino-4-methoxy-2-methylpheno; 2-dimethylamino-5-aminopyridine; 2,4,5,6-tetra-aminopyrimidine; 4,5-diamino-1-methylpyrazole; 1-phenyl-3-methyl-5-pyrazolone; 6-methoxy-8-aminoquinoline; 2,6-dihydroxy-4-methylpyridine; 5-hydroxy-1,4-benzodioxane; 3,4-methylenedioxyphenol; 4-hydroxyethylamino-1,2- methylenedioxybenzene; 2,6-dihydroxy-3,4-dimethylpyridine; 5-chloro-2,3-dihydroxypyridine; 3,5-diamino-2,6-dimethoxypyridine; 2-hydroxyethylamino-6-methoxy-3-aminopyridine; 3,4-methylenedioxyaniline; 2,6-bis-hydroxyethoxy-3,5-diaminopyridine; 4-hydroxyindole; 3-amino-5-hydroxy-2,6-dimethoxypyridine; 5,6-dihydroxyindole; 7-hydroxyindole; 5-hydroxyindole; 2-bromo-4,5-methylenedioxyphenol; 6-hydroxyindole; 3-amino-2-methylamino-6-methoxypyridine; 2-amino-3-hydroxypyridine; 2,6-diaminopyridine; 5-(3;5-diamino-2-pyridyloxy)-1,3-dihydroxypentane; 3-(3,5-diamino-2-pyridyloxy)-2-hydroxypropanol; 4-hydroxy-2,5,6-triaminopyrimidine, and mixtures thereof.

14. A method for permanently coloring hair which comprises contacting the hair with a composition in accordance with claim 1.

* * * * *